(12) United States Patent
Waldorf et al.

(10) Patent No.: US 7,357,507 B2
(45) Date of Patent: Apr. 15, 2008

(54) IMAGE-BASED SYSTEM TO OBSERVE AND DOCUMENT EYE RESPONSES

(75) Inventors: Ronald Waldorf, Beverly Hills, CA (US); Barbara Mauch, Inglewood, CA (US)

(73) Assignee: VisioNetx, Inc., Centennial, CO (US)

( * ) Notice: Subject to any disclaimer, the term of this patent is extended or adjusted under 35 U.S.C. 154(b) by 199 days.

(21) Appl. No.: 11/398,009

(22) Filed: Apr. 5, 2006

(65) Prior Publication Data

US 2007/0236662 A1     Oct. 11, 2007

(51) Int. Cl.
*A61B 3/14* (2006.01)
(52) U.S. Cl. ............... 351/206; 351/210; 351/221
(58) Field of Classification Search ............... 351/200, 351/205, 206, 209, 210, 221
See application file for complete search history.

(56) References Cited

U.S. PATENT DOCUMENTS 4,993,825 A * 2/1991 Abe et al. ............... 351/210

2004/0218144 A1 * 11/2004 Silverbrook et al. ........ 351/205

\* cited by examiner

*Primary Examiner*—Huy K Mai
(74) *Attorney, Agent, or Firm*—Patton Boggs LLP

(57) ABSTRACT

The image-based system is used to observe and document eye responses which can be used to implement the procedures defined in the Standardized Field Sobriety Test as well as the Drug Recognition Expert Program. These eye responses include pupil movement as well as pupil size and responses, for either one or both eyes simultaneously. The system includes a headset against which the subject places their face. The faceplate has two eye openings through which illumination devices transmit beams of infrared light to illuminate the subject's eyes. Two imaging devices are mounted on the headset opposite the eye openings to generate images of the subject's illuminated eyes. The generated images are transmitted to an image recording device for storage and an image display device for display to a test administrator.

16 Claims, 6 Drawing Sheets

IMAGE-BASED SYSTEM TO OBSERVE AND DOCUMENT EYE RESPONSES

FIELD OF THE INVENTION

This invention relates to determining the level of impairment of a subject and, in particular, to an apparatus that can be used to implement the measurement of a subject's eye gaze tracking and the monitoring of the subject's eye behavior.

BACKGROUND OF THE INVENTION

It is a problem to determine whether a subject is impaired due to the use of alcohol or drugs, or whether the subject is suffering from sleep deprivation and/or a medical condition that could cause impairment. This impairment determination can be reliably accomplished by the measurement of eye gaze tracking and the monitoring of eye behavior (e.g., pupil size, blink rate, gaze, etc.) to determine a subject's alertness and attention.

For the detection of impairment, law enforcement officers in the field presently ask the subject to direct their gaze at a target which follows a predefined pattern defined by the Standardized Field Sobriety Test and/or Drug Recognition Expert protocols as established by the National Highway Traffic Safety Administration USA). By tracking the eye movements and measuring the pupil size and its responses, it is possible to determine a subject's impairment status. For instance, a subject who has been smoking marijuana demonstrates a very slow pupil reaction to abrupt changes in lighting conditions, where the pupil regains a dilated state even under bright light, sometimes called "rebound dilation". While under the influence of heroin, the subject's pupil remains fully constricted, even in the dark, i.e., pinpoint pupil If a subject has been drinking alcohol, their eye movements become "jerky" on movements to the right or left, i.e. "lack of smooth pursuit". Upon lateral gaze, they can also exhibit a constant "jerk", called horizontal gaze nystagmus (HGN). Therefore, the tracking of changes in the pupil's centroid location and/or size and reaction to light changes can be used to indicate impairment.

With all of these metrics, the accurate observation, tracking and measurement of the subject's pupil centroid and area is critical to the determination of impairment. It is also important in some applications to observe and detect eye blinking in order to compute the eye blinking rate to determine drowsiness and to ensure that pupil measurements are not computed at those time instances when a blink occurs, since the pupil is either partially visible or not visible at all when a blink occurs.

Presently, all of these measurements are typically performed manually with the accuracy and reliability of these measurements being subjective and possibly tainted by the ambient conditions under which the test is administered. Ambient conditions include the inability to maintain the subject's gaze in a fixed direction, erratic lighting conditions, and the subjective nature of the test administrator's administration of the test. Alternatively, standard methods of video taping of the eye responses for the Standardized Field Sobriety Test have been used, such as having one camera mounted on a tripod or handheld and aimed at the subject, but these applications can also be tainted by the ambient conditions under which the test is administered, further including camera aiming and maintaining a steady video image when the video camera is handheld.

BRIEF SUMMARY OF THE INVENTION

The above-described problems are solved and a technical advance achieved by the present image-based system to observe and document eye responses which can be used to implement the procedures defined in the Standardized Field Sobriety Test as well as the Drug Recognition Program. These eye responses include pupil movement as well as pupil responses to illumination and target tracking for either eye or both eyes simultaneously.

The image-based system to observe and document eye responses includes a headset that has a faceplate against which the subject places their face. The faceplate has a single large opening through which illumination devices transmit beams of infrared light to illuminate the subject's eyes. Another embodiment of the system can be two openings in which the illumination transmits to each eye. In this embodiment, two imaging devices are mounted on the headset opposite the eye opening(s) to generate images of the subject's illuminated eyes. It is conceivable that other embodiments could use a single or multiple imaging devices. The generated images are transmitted to an image recording device for storage and to an image display device for display to a test administrator. The test administrator is able thereby to view the subject's eye(s) while providing the stimulus target (finger, pen tip, etc.) for the subject to view through the eye opening(s) of the faceplate. The subject's eye responses, in tracking the stimulus target as it is moved by the test administrator, are recorded on an image recording device along with audio annotations from the test administrator. This system allows for playback of the eye responses and associated audio for review and training purposes. The use of infrared illumination of the subject's eyes further enhances the observation, as well as the documentation and review of the eye movement and pupil responses, especially in those individuals with dark pigmented irises. In addition, a data processing system may optionally be used to perform an analysis of the image generated by the imaging devices to quickly and accurately localize the pupil's boundaries, area, and center coordinates in close-up video imagery of the subject's eyes as captured with the imaging devices.

The use of the headset increases the accuracy and reliability of these measurements and allows for testing even in low light or totally dark environments, which is sometimes the case in law enforcement applications. Thus, this system can be used both in a classroom environment for training purposes and in the field by law enforcement officers for testing individuals who are stopped for suspicion of Driving Under the Influence (DUI) or Driving While Impaired (DWI).

DETAILED DESCRIPTION OF THE INVENTION

In determining whether a subject is impaired due to the use of alcohol or drugs, or whether the subject is suffering from sleep deprivation or other medical impairing condition, the measurement of eye gaze tracking and the monitoring of eye behavior (e.g., blink rate, gaze, etc.) can be used to determine a subject's alertness and attention.

The accuracy and reliability of these measurements are subjective and can be tainted by the ambient conditions under which the test is administered. Ambient conditions include the inability to maintain the subject's gaze in a fixed direction, erratic lighting conditions, and the subjective nature of the test administrator's administration of the test.

System Characteristics

In order to minimize the impact of ambient conditions, the present image-based system to observe and document eye responses includes a headset that has a faceplate against which the subject places their face. The headset increases the accuracy and reliability of these measurements and reduces any inaccuracy occasioned by the ambient conditions under which the test is administered.

The faceplate has a single or two eye openings through which illumination devices transmit beams of infrared light to illuminate the subject's eyes. Two imaging devices (more or less in other embodiments) are mounted on the headset opposite the eye opening(s) to generate an image or images of the subject's illuminated eyes. The generated images are transmitted to an image recording device for storage and an image display device for display to a test administrator. The test administrator is able thereby to view the subject's eye(s) while providing the stimulus target (finger, pen tip, etc.) for the subject to view through the eye openings of the faceplate. The subject's eye responses are recorded on an image recording device along with audio annotation from the test administrator. This system allows for playback of the eye responses and associated audio for review and training purposes. The use of infrared illumination further enhances the observation, as well as the documentation and review of the eye movement and pupil responses, especially in those individuals with dark pigmented irises.

System Block Diagram

Figure 1:
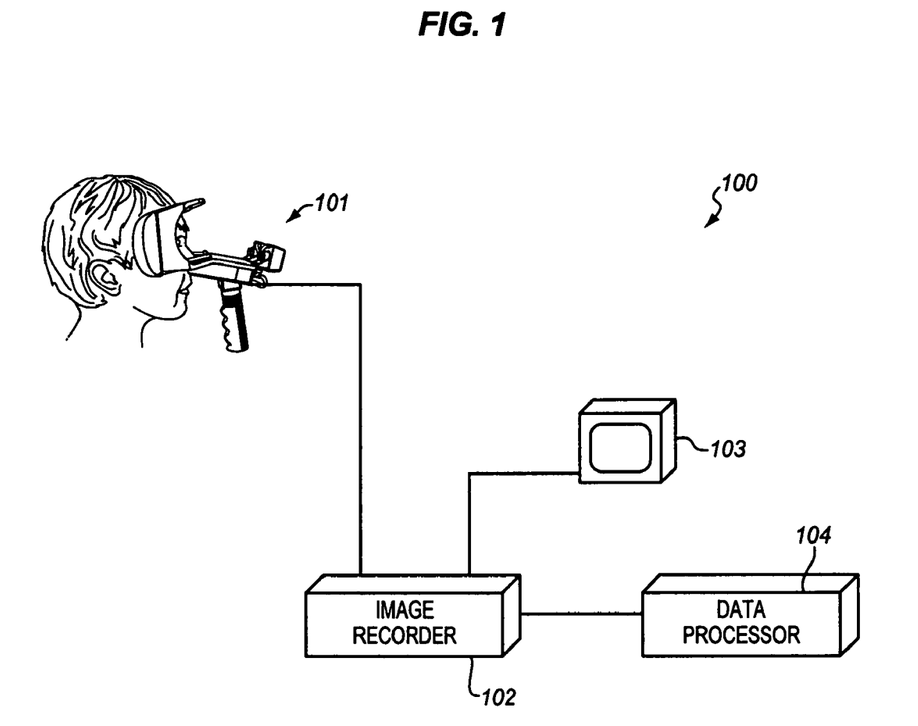
FIG. 1 illustrates a block diagram of the present image-based system to observe and document eye responses.

FIG. 1 illustrates a block diagram of the present image-based system to observe and document eye responses 100 (with additional details shown in FIGS. 2-6), where a headset 101 is used to administer the test to the subject. The headset 101 includes illumination devices 111-114 and imaging devices 121, 122 that are attached to a frame 131, which includes a faceplate 141 to position the subject's face with respect to illumination devices 111-114 and imaging devices 121, 122. A source of electrical power, such as batteries, is provided to power illumination devices 111-114 and imaging devices 121, 122, with the batteries located in the grip portion 151 of the headset 101. The imaging devices 121, 122 are connected to an image recording device 102, such as a video recorder, DVD recorder, computer, or other such apparatus for capturing and storing image data. The interconnection between the headset 101 and the image recording device 102 can be wired or wireless, using a cable 171 or wireless communication protocol, respectively. An image display device 103 is also provided to present a real time representation to a test administrator of the image generated by the imaging devices 121, 122, and the image display device 103 typically is connected to the image recording device 102 (and/or imaging devices) via a wired or wireless connection.

In addition, a data processing system 104 may optionally be used to perform an analysis of the image generated by the imaging devices 121, 122 to quickly and accurately localize the pupil's boundaries, area, and center coordinates in close-up video imagery of the subject's eye(s) as captured with imaging devices 121, 122. The data processing system 104 of the image-based system to observe and document eye responses 100 can also use a region growing algorithm or other image processing technique to extract and track the centroid location and area of the subject's pupil under difficult conditions, such as blinking, eyelid droop, head movement, eye gaze at the extreme corners of the eyes, presence of heavy eye makeup, and where light specularities occur in or near the pupil region. The use of a data processing system 104 eliminates any subjectivity on the part of the test administrator and reduces the possibility of errors due to the degree of precision in the measurement of the subject's eye gaze tracking and the monitoring of the subject's eye behavior.

Headset Implementation

Figure 2:
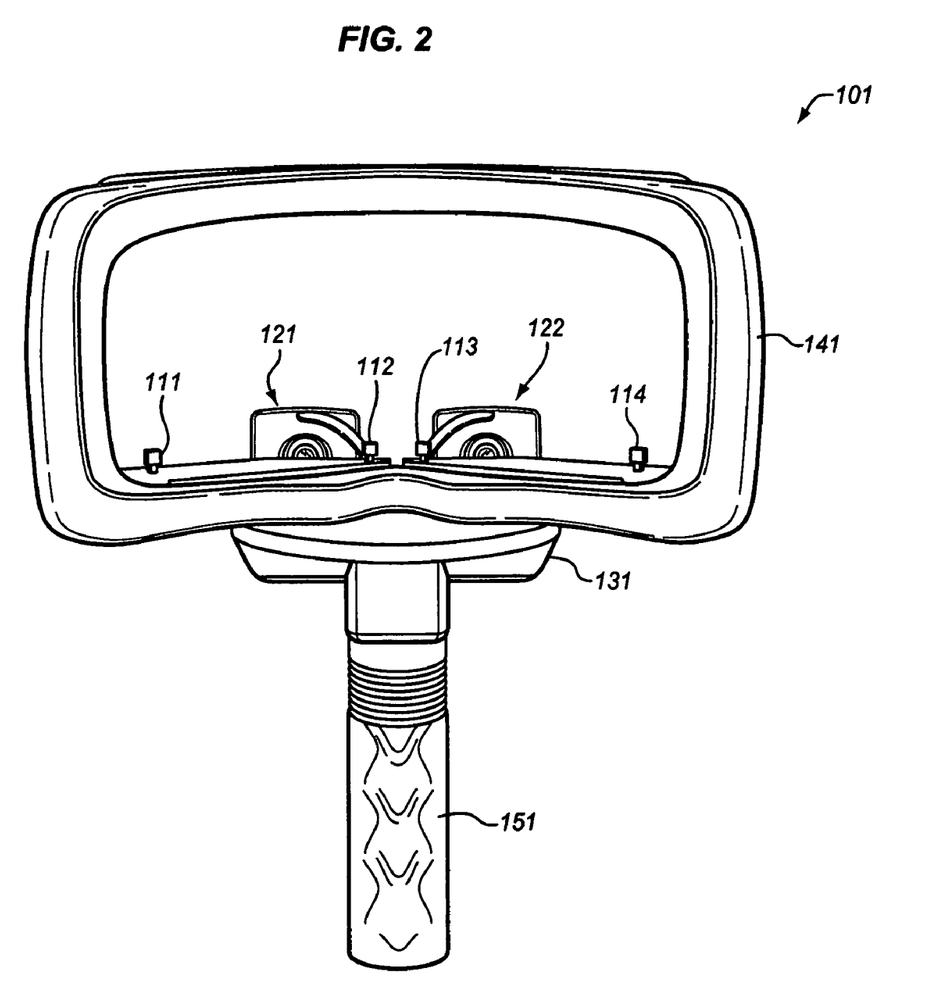
FIGS. 2-4 illustrate rear, top, and side views, respectively, of the headset of the present image-based system to observe and document eye responses.
Figure 3:
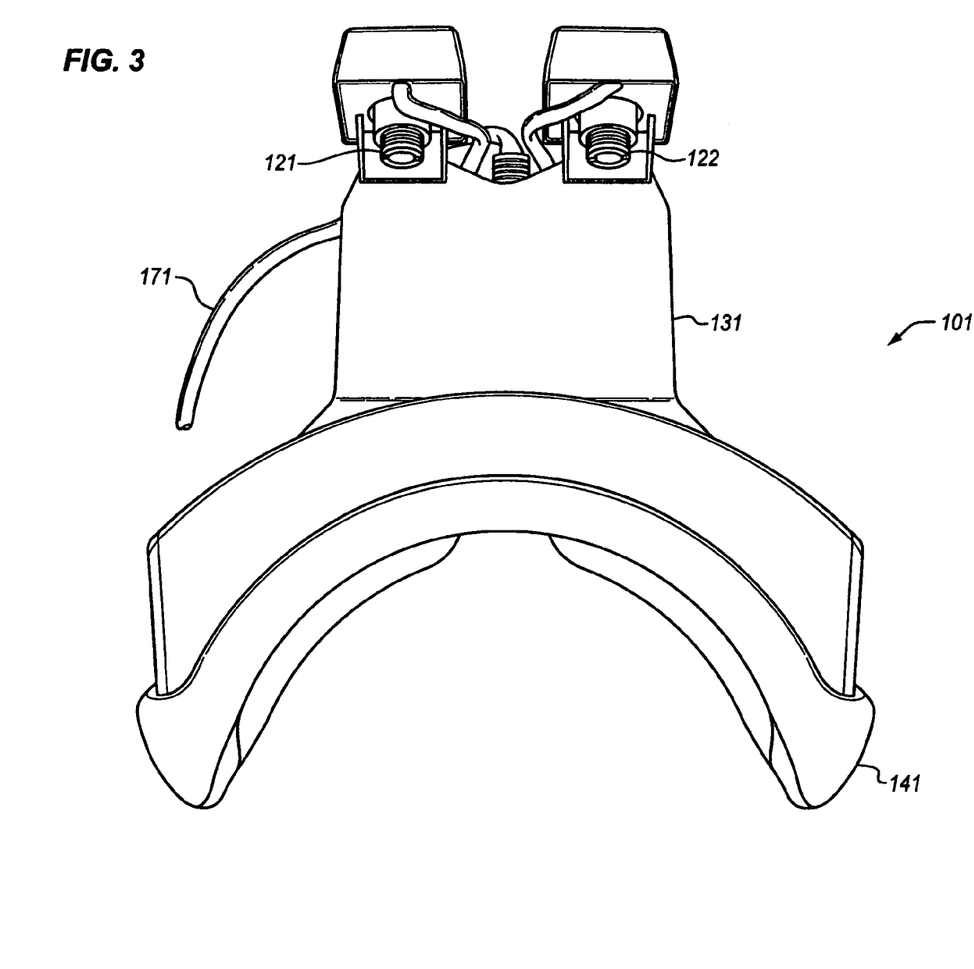
Figure 4:
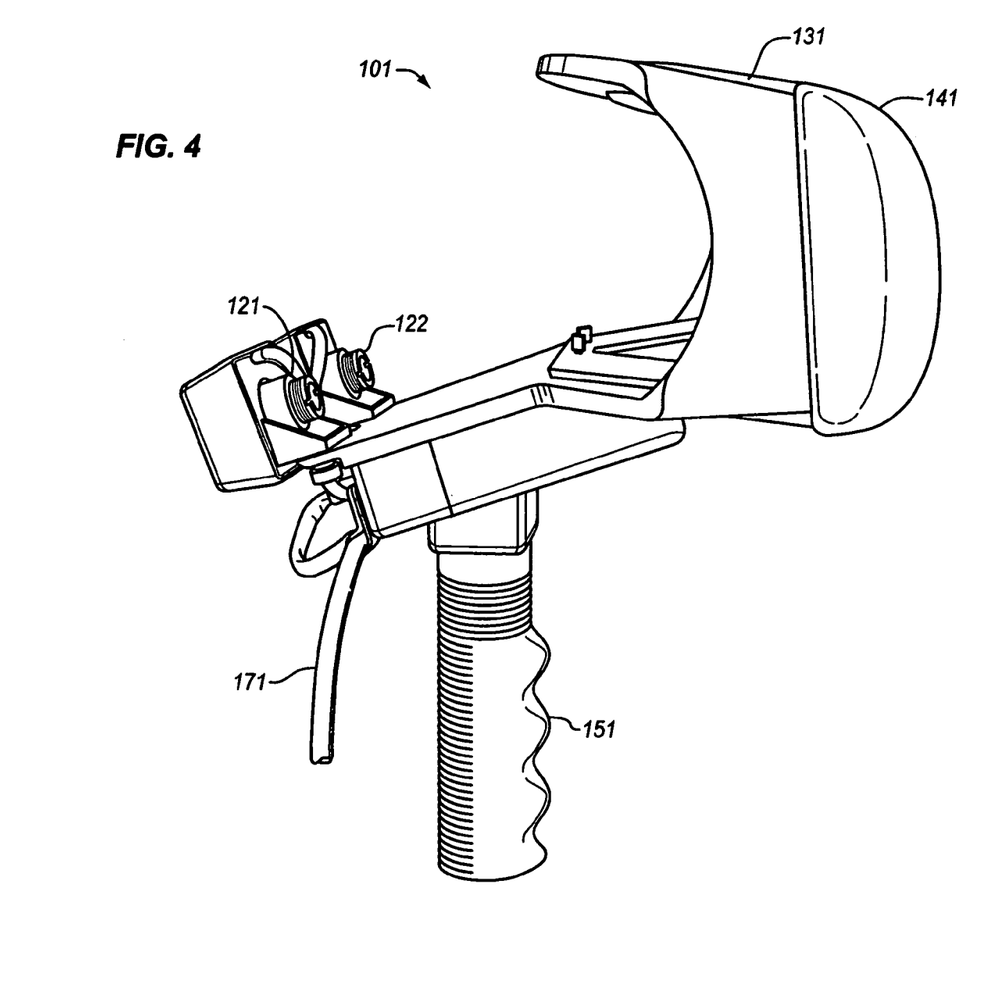
Figure 5:
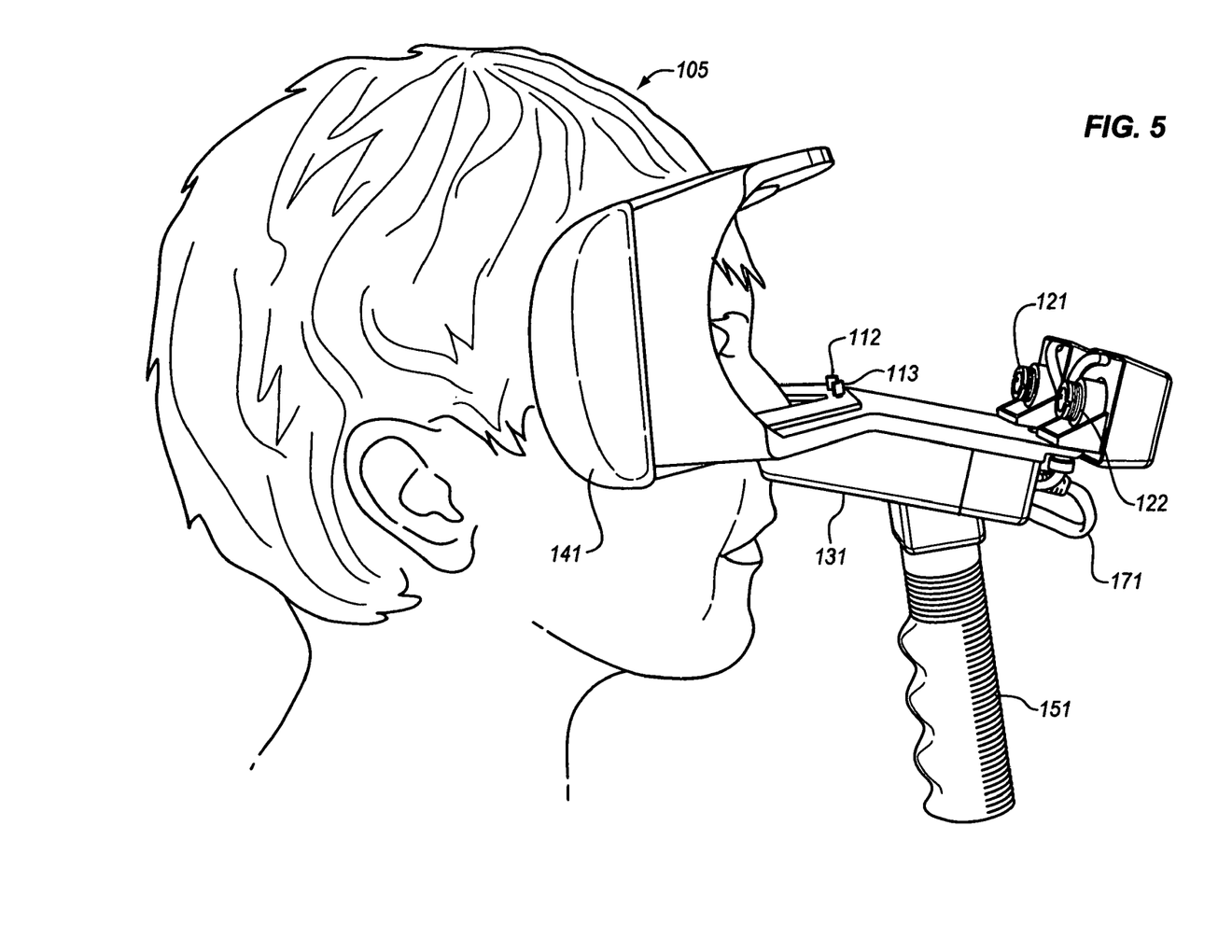
FIGS. 5 and 6 illustrate side and front views, respectively, of the headset of the present image-based system to observe and document eye responses as used by a subject.
Figure 6:
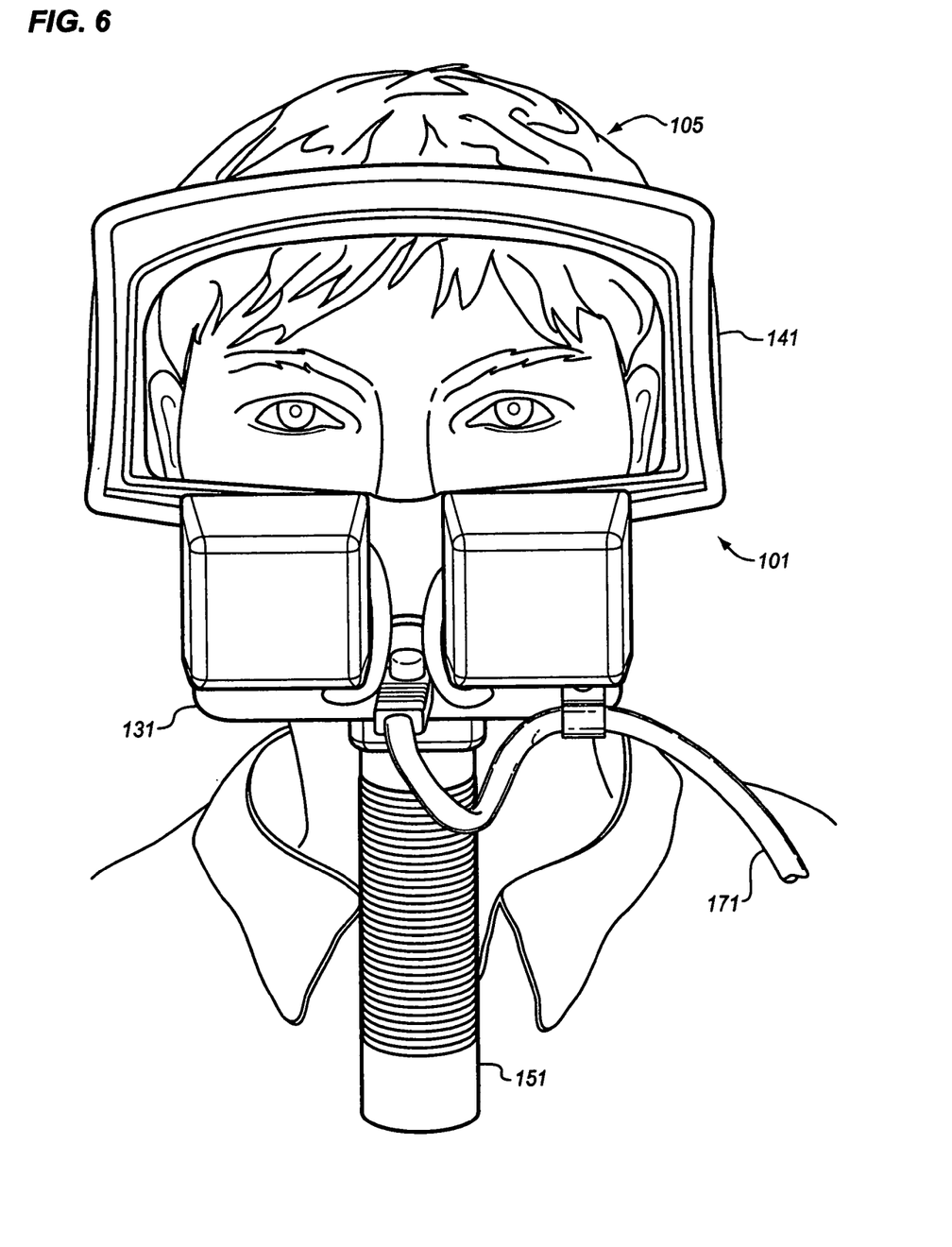

FIGS. 2-4 illustrate rear, top, and side views, respectively, of the headset 101 of the present image-based system to observe and document eye responses 100; and FIGS. 5 and 6 illustrate side and front views, respectively, of the headset 101 of the present image-based system to observe and document eye responses 100 as used by a subject 105.

The headset 101 is the base user interface structure of the present image-based system to observe and document eye responses 100. The headset 101 is based on a frame 131 to which the various elements are attached. A faceplate 141 is attached to the frame 131, shaped to substantially conform to a subject's face and having two eye openings 142, 143 oriented opposite a subject's eyes when the subject places their face against faceplate 141. A chin rest (not shown) can optionally also be provided to assist in the alignment of the subject's face with the eye openings 142, 143.

Attached to frame 131 are two imaging devices 121, 122, such as image cameras of the Charge Coupled Device type (or other functional equivalent), one that provides an image of the right eye and the other of the left eye. The image that is generated is typically captured at a rate of 30 frames/sec, at a frame size of 320×240, and at a grayscale resolution of 8 bits. The resultant image provides adequate data for the proper determination of eye gaze tracking and the monitoring of eye behavior. The orientation of the imaging devices 121, 122 can be adjusted to place the eyes in the center of the image that is displayed on the image display device 103. The image display device 103 can be of the quad-type, meaning that each eye is displayed in one of four image quadrants on the screen of the image display device 103—typically next to each other on the upper horizontal or lower horizontal aspect ratio to give an image as if the eyes were seen as normal, adjacent to each other.

The faceplate 131 contains illumination devices 111-114, such as infrared Light Emitting Diodes, for the illumination of the subject's eyes. Two light emitting diodes can be used in or adjacent to each eye opening 132, 133 to ensure proper illumination of the subject's eyes. These infrared Light Emitting Diodes produce invisible illumination. One unique attribute of the infrared illumination is the visual observational enhancement of the CCD image of the eye for dark-iris individuals.

A separate wireless microphone system 161 allows for the verbal annotation of remarks either from the subject or the test administrator onto the image recording device 102. It is contemplated that microphone 161 can be built into headset 101. It is also contemplated that headset 101 is wireless, meaning that the image data as well as the audio component would be transmitted from headset 101 to image recording device 102 in a wireless mode; no connection from a hard-wired cable would be necessary.

Additional Functionality

An added benefit provided by the present image-based system to observe and document eye responses is that test administrators, including Law Enforcement Officers who are being trained and certified in the skills of observing the eye signs associated with the Standardized Field Sobriety Test as well as the Drug Recognition Expert Program programs, have had little opportunity to review images of eye signs of impaired subjects during their training sessions. The ability to review actual image data from impaired subjects, gathered under real world field conditions, enhances the training of these officers by allowing them to review their observations and comments with their instructors. Having these responses displayed and recorded with an enhanced image system makes this task that much easier and meaningful.

A further benefit is the ability to preserve the real time image data that is collected in the field for presentation and review at a later time. The optional data processing system can provide a precise analysis of this data, both in the field and at a later time, to perform an analysis of the image generated by the imaging devices, to quickly and accurately localize the pupil's boundaries, area, and center coordinates in close-up video imagery of the subject's eyes as captured with the imaging devices.

SUMMARY

The image-based system to observe and document eye responses includes a headset against which the subject places their face. The faceplate has two eye openings through which illumination devices transmit beams of infrared light to illuminate the subject's eyes. Two imaging devices are mounted on the headset opposite the eye openings to generate images of the subject's illuminated eyes. The generated images are transmitted to an image recording device for storage and an image display device for display to a test administrator.

What is claimed as new and desired to be protected by Letters Patent of the United States is:

1. An image-based system to observe and document eye responses, comprising:
   a frame;
   a faceplate attached to said frame, shaped to substantially conform to a subject's face and having at least one opening oriented opposite a subject's eyes when said subject places their face against said faceplate;
   at least one illumination device attached to said frame and aligned with said eye opening to illuminate a subject's eyes when said subject places their face against said faceplate; and
   at least one imaging device attached to said frame and aligned with said eye openings to generate an image of a subject's eyes when said subject places their face against said faceplate.

2. The image-based system to observe and document eye responses of claim 1 further comprising:
   an image recording device connected to said at least one imaging device for recording images generated by said at least one imaging device.

3. The image-based system to observe and document eye responses of claim 2 wherein said image recording device comprises:
   a digital data recording device for storing image data from the class of digital recording devices including: video tape recorder, DVD recorder, computer system, and data memory device.

4. The image-based system to observe and document eye responses of claim 2 further comprising:
   an image display device connected to at least one of said at least one imaging device and said image recording device for displaying said image of a subject's eyes when said subject places their face against said faceplate.

5. The image-based system to observe and document eye responses of claim 1 further comprising:
   a power source for providing power to said at least one illumination device and said at least one imaging device.

6. The image-based system to observe and document eye responses of claim 1 further comprising:
   a handle attached to said frame for enabling a user to position said faceplate against said subject's face.

7. The image-based system to observe and document eye responses of claim 6 further comprising:
   wherein said handle includes a compartment for housing a power source for providing power to said at least one illumination device and said at least one imaging device.

8. The image-based system to observe and document eye responses of claim 1 wherein said at least one illumination device comprises:
   infrared source for illuminating said subject's eyes with light in the infrared spectrum.

9. The image-based system to observe and document eye responses of claim 2 further comprising:
   data processing system, connected to at least one of said at least one imaging device and said image recording device, for processing said image of a subject's eyes when said subject places their face against said faceplate to measure said subject's eye gaze tracking and eye behavior in response to tracking a stimulus target.

10. The image-based system to observe and document eye responses of claim 1 further comprising:
    a cable for interconnecting said image recording device to said at least one imaging device.

11. An image-based system to observe and document eye responses, comprising:
    a frame;
    a faceplate attached to said frame, shaped to substantially conform to a subject's face and having at least one opening oriented opposite a subject's eyes when said subject places their face against said faceplate;
    at least one infrared light emitting diode illumination device attached to said frame and aligned with said at least one eye opening to illuminate a subject's eyes when said subject places their face against said faceplate;
    at least one imaging device attached to said frame and aligned with said at least one eye opening to generate an image of a subject's eyes when said subject places their face against said faceplate; and
    an image display device connected to said imaging device for displaying said image of a subject's eyes when said subject places their face against said faceplate.

12. The image-based system to observe and document eye responses of claim 11 further comprising:

an image recording device connected to said at least one imaging device for recording images generated by said at least one imaging device.

13. The image-based system to observe and document eye responses of claim 11 further comprising:
a power source for providing power to said at least one illumination device and said at least one imaging device.

14. The image-based system to observe and document eye responses of claim 11 further comprising:
a handle attached to said frame for enabling a user to position said faceplate against said subject's face.

15. The image-based system to observe and document eye responses of claim 14 further comprising:
wherein said handle includes a compartment for housing a power source for providing power to said at least one illumination device and said at least one imaging device.

16. The image-based system to observe and document eye responses of claim 11 further comprising:
a chin rest attached to said frame to align said subject's face with said at least one eye opening.

* * * * *